(12) United States Patent
Cipolli et al.

(10) Patent No.: US 8,997,784 B2
(45) Date of Patent: Apr. 7, 2015

(54) ELECTRONIC FLUID FLOW CONTROLS WITH INTEGRATED MANUAL FLUID FLOW CONTROLS

(71) Applicant: Mindray DS USA, Inc., Mahwah, NJ (US)

(72) Inventors: Richard G. Cipolli, Nanuet, NY (US); David Gibson, Forest Hill, MD (US)

(73) Assignee: Shenzhen Mindray Bio-Medical Electronics Co. Ltd., Shenzhen (CN)

( * ) Notice: Subject to any disclaimer, the term of this patent is extended or adjusted under 35 U.S.C. 154(b) by 293 days.

(21) Appl. No.: 13/677,098

(22) Filed: Nov. 14, 2012

(65) Prior Publication Data

US 2014/0130801 A1 May 15, 2014

(51) Int. Cl.
| | |
|---|---|
| *F16K 11/00* | (2006.01) |
| *F16K 31/06* | (2006.01) |
| *F16K 31/44* | (2006.01) |
| *A61M 16/12* | (2006.01) |
| *F16K 11/20* | (2006.01) |
| *F16K 11/24* | (2006.01) |
| *F16K 11/22* | (2006.01) |
| *A61M 16/00* | (2006.01) |
| *A61M 16/01* | (2006.01) |
| *A61M 16/10* | (2006.01) |
| *A61M 16/18* | (2006.01) |
| *A61M 16/20* | (2006.01) |
| *F17D 3/01* | (2006.01) |

(52) U.S. Cl.
CPC ............... *A61M 16/12* (2013.01); *A61M 16/18* (2013.01); *A61M 16/20* (2013.01); *F16K 11/20* (2013.01); *F17D 3/01* (2013.01); *F16K 11/24* (2013.01); *F16K 11/22* (2013.01); *A61M 16/0051* (2013.01); *A61M 16/01* (2013.01); *A61M 16/104* (2013.01); *A61M 2016/0039* (2013.01); *A61M 2205/505* (2013.01)

(58) Field of Classification Search
CPC ......... F16K 11/20; F16K 11/22; F16K 11/24; F17D 3/01
USPC .................. 137/606, 601.14, 599.06–599.09; 251/129.03, 129.04; 128/203.15
See application file for complete search history.

(56) References Cited

U.S. PATENT DOCUMENTS

| | | | | |
|---|---|---|---|---|
| 3,021,840 | A * | 2/1962 | Hallamore et al. ...... | 128/200.21 |
| 5,050,062 | A * | 9/1991 | Hass .............................. | 700/32 |
| 5,806,513 | A * | 9/1998 | Tham et al. ............... | 128/204.22 |
| 6,024,087 | A * | 2/2000 | Kersey et al. ............ | 128/203.12 |
| 6,360,762 | B2 * | 3/2002 | Kitayama et al. ................. | 137/1 |
| 6,823,535 | B2 * | 11/2004 | Tomita et al. ..................... | 4/425 |

(Continued)

*Primary Examiner* — Craig Schneider
*Assistant Examiner* — Seth W Mackay-Smith (57) ABSTRACT

In various embodiments, a flow selector of a fluid flow control system may be used to select a flow rate of a fluid. When the system is in an electronic mode, an encoder may electronically encode the fluid flow selection. A controller may receive the electronically encoded flow selection and transmit a corresponding control signal to an electronic valve to allow the fluid to flow at the selected flow rate. An engagement device, such as a clutch, may disengage the flow selector from a mechanical valve when the fluid flow control system enters a manual mode. When the system is in a manual mode, the engagement device may engage the flow selector with the mechanical valve, allowing the flow selector to directly control the flow rate of the fluid through the mechanical valve. Applications to gases and anesthesia delivery are disclosed herein. Various alternative components and embodiments are described herein.

13 Claims, 6 Drawing Sheets

(56) References Cited

U.S. PATENT DOCUMENTS

| | | | |
|---|---|---|---|
| 6,857,443 B2* | 2/2005 | Volgyesi | 137/101.19 |
| 7,438,072 B2* | 10/2008 | Izuchukwu | 128/203.15 |
| 7,624,757 B2* | 12/2009 | Schmitt | 137/606 |
| 7,673,645 B2* | 3/2010 | Ding et al. | 137/9 |

* cited by examiner

ELECTRONIC FLUID FLOW CONTROLS WITH INTEGRATED MANUAL FLUID FLOW CONTROLS

TECHNICAL FIELD

This disclosure generally relates to controlling the flow of fluids via manually adjustable controls. Particularly, this disclosure relates to fluid flow controls that can be used for both electronic control and for backup manual control.

SUMMARY

In various instances, the rates of flow of fresh gases, such as oxygen, nitrous oxide, and air, in modern anesthesia delivery systems may be controlled by a practitioner either electronically or mechanically. In various embodiments, one or more control knobs may be configured to electronically control a flow rate of a gas when in an electronic mode, and automatically provide manual backup control of the flow rate of the gas when in a manual mode. In one embodiment, a normally-open valve may feed a gas from a gas supply to a mechanically operated needle valve. A normally-closed valve may feed the gas from the gas supply to an electronically operated proportional valve. When the gas flow control system is in an electronic mode, the normally-open valve may be closed and the normally-closed valve may be opened, directing the gas to the electronic proportional valve.

A knob, or other flow selector, may be manually adjusted by a practitioner to select a flow rate of the gas. In an electronic mode, an encoder, such as a rotary encoder, may electronically encode the gas flow selection made via the knob (or other flow selector). A controller may received the electronically encoded flow selection and transmit a corresponding control signal to the electronic proportional valve.

An engagement device, such as a clutch, may disengage the knob from the mechanically operated needle valve when the gas flow control system is in an electronic mode to prevent unwanted adjustment. When the gas flow control system is in a manual mode, the clutch may engage the knob with the mechanically operated needle valve, the normally-open valve may allow the gas to flow to the needle valve, and the normally-closed valve may prevent gas from flowing to the electronic proportional valve.

In an alternative embodiment, a single needle valve may be electronically controlled when a gas flow control system is powered and manually controlled when a gas flow control system is not powered. The number of gases, types of gases, and uses for the gas flow control system may vary by application. Additionally, fluids other than gases, such as liquids, may also be utilized in conjunction with the various embodiments described herein.

DETAILED DESCRIPTION

While electronic flow control of gases may be useful during anesthesia delivery, it may be desirable to provide manual backup controls as well. For example, in the event of power loss, electronic failure, mechanical failure, and/or based on a user selection of a manual mode, it may be desirable to continue supplying gases during anesthesia delivery. In some embodiments, electronic controls, such as trim knobs used in conjunction with encoders may facilitate the electronic adjustment of the flow rate of one or more gases during anesthesia delivery. Separate backup knobs may be available for use in the event of power failure or power unavailability. In such embodiments, the practitioner may need to engage the backup knobs, switch the machine from an electronic mode to a manual mode, and/or ensure that the manual knobs are set to a desirable state prior to switching to a manual mode.

Power loss during anesthesia delivery may be a confusing and/or disruptive time during a critical medical procedure. It may be an inconvenience and/or confusing for a practitioner to switch from using a set of electronic knobs and controls to a set of manual knobs or controls. In various embodiments of the present disclosure, flow selectors, such as rotary knobs, may be electronically operable when a fluid flow control system is in an electronic mode and manually operable when a fluid flow control system is in a manual mode. Accordingly, a practitioner may continue to use the same control knobs to adjust the flow rate of one or more fluids regardless of whether the fluid flow control system is powered or not.

The number of diversion valve systems, mechanically operated valves, electronically operated valves, controllers, encoders, flow selectors, and/or other components described herein may correspond to the number of gases (or liquids) available. In various anesthesia delivery systems, oxygen, nitrous oxide, and/or air may each be independently controllable and/or proportionally controllable. A mixture of one or more gases may be used in conjunction with a vaporizer to deliver anesthesia.

According to various embodiments, a user may select a flow rate of a combination of oxygen and air to be supplied to a patient. A user may also select a flow rate of nitrous oxide to be provided to a patient instead of air. In some embodiments, the nitrous oxide may be supplied in addition to air. Regardless of the selections made by a user, a safe amount of oxygen may be automatically supplied to the patient, as ensured by an oxygen ratio controller (ORC) when in an automatic mode.

In one embodiment, a diversion valve system may direct the flow of a gas (or liquid) from a gas supply to either a mechanical flow control valve, such as a mechanically operated needle valve, or an electronic flow control valve, such as an electronic proportion valve, depending on whether or not the system has power. Regardless of the power state, the practitioner may use a flow selector, such as a knob, to select a flow rate of each available gas.

If the system is in an electronic mode, the selected flow rate may be encoded and transmitted to a controller. The controller may then send a control signal to the electronic proportion valve in order to achieve the selected flow rate. When the system is in an electronic mode, a clutch, or other engagement device, may prevent the flow selector from actuating the mechanically operated needle valve.

If the system is in a manual mode, the clutch may mechanically engage the flow selector with the mechanically operated needle valve, such that the selected flow rate is mechanically translated from the flow selected to the needle valve to achieve the selected flow rate.

According to various embodiments, the diversion valve system may include normally-open and normally-closed valves in order to selectively prevent the gas from flowing to both the mechanically operated needle valve and the electronic proportion valve. The diversion valve system may be implemented using any of a wide variety of valves and/or control systems, such as a three-way selector valve.

In some embodiments, the diversion valve system may be omitted. For example, in a manual mode, the flow selector may directly engage and mechanically operate a needle valve. In an electronic mode, a selection made by a flow selector may be encoded by an encoder and an electronic controller may provide control instructions to a stepper motor to mechanically operate the same needle valve. In such an embodiment, the needle valve may be considered the mechanical flow control valve and the same needle valve in combination with the electronic stepper motor may be considered the electronic flow control valve. As in other embodiments, a clutch or other engagement device may mechanically disengage the flow selector (e.g., knob) from the needle valve when the system is in an electronic mode. In some embodiments, a clutch or other engagement device may mechanically disengage the stepper motor from the needle valve when the system is in a manual mode.

In various embodiments, the flow selector may comprise any of a wide variety of knobs, buttons, rotatable actuators, slides, and/or other analog and/or digital selection devices. In various embodiments, a controller or control system may be implemented as any combination of hardware, firmware, and/or software. For example, a controller may be implemented as a field-programmable gate array (FPGA). In some embodiments, an electronic controller for transmitting a control signal to an electronic flow control valve may be distinct from other electronic components in a gas flow control system, such as microprocessors and other electronic components associated with displays, touch screens, data storage, data connectivity, etc. The reliability of the electronic flow controls may be improved by separating the electronic flow controls from other electronic features of an anesthesia delivery device and/or by implementing it in hardware rather than software.

While the various examples and embodiments disclosed herein are described in conjunction with a gas flow control system, many of the embodiments could be used or modified for use with any type of fluid, including various gases and liquids. Gases used for anesthesia delivery, such as oxygen, nitrous oxide, and air, are used herein as examples of gases that can be controlled via the presently described fluid flow control systems and are referred to as gas flow control systems.

Some of the infrastructure that can be used with embodiments disclosed herein is already available, such as general-purpose computers, computer programming tools and techniques, digital storage media, and communication networks. A computing device or other electronic controller may include a processor, such as a microprocessor, a microcontroller, logic circuitry, and/or the like. The processor may include a special purpose processing device such as application-specific integrated circuits (ASIC), programmable array logic (PAL), programmable logic array (PLA), a programmable logic device (PLD), FPGA, or another customizable and/or programmable device. The computing device may also include a machine-readable storage device, such as non-volatile memory, static RAM, dynamic RAM, ROM, CD-ROM, disk, tape, magnetic, optical, flash memory, or other machine-readable storage medium. Various aspects of certain embodiments may be implemented using hardware, software, firmware, or a combination thereof.

The embodiments of the disclosure will be best understood by reference to the drawings, wherein like parts are designated by like numerals throughout. The components of the disclosed embodiments, as generally described and illustrated in the figures herein, could be arranged and designed in a wide variety of different configurations. Furthermore, the features, structures, and operations associated with one embodiment may be applicable to or combined with the features, structures, or operations described in conjunction with another embodiment. In other instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments. In addition, the steps of a method do not necessarily need to be executed in any specific order, or even sequentially, nor do the steps need to be executed only once.

Figure 1:
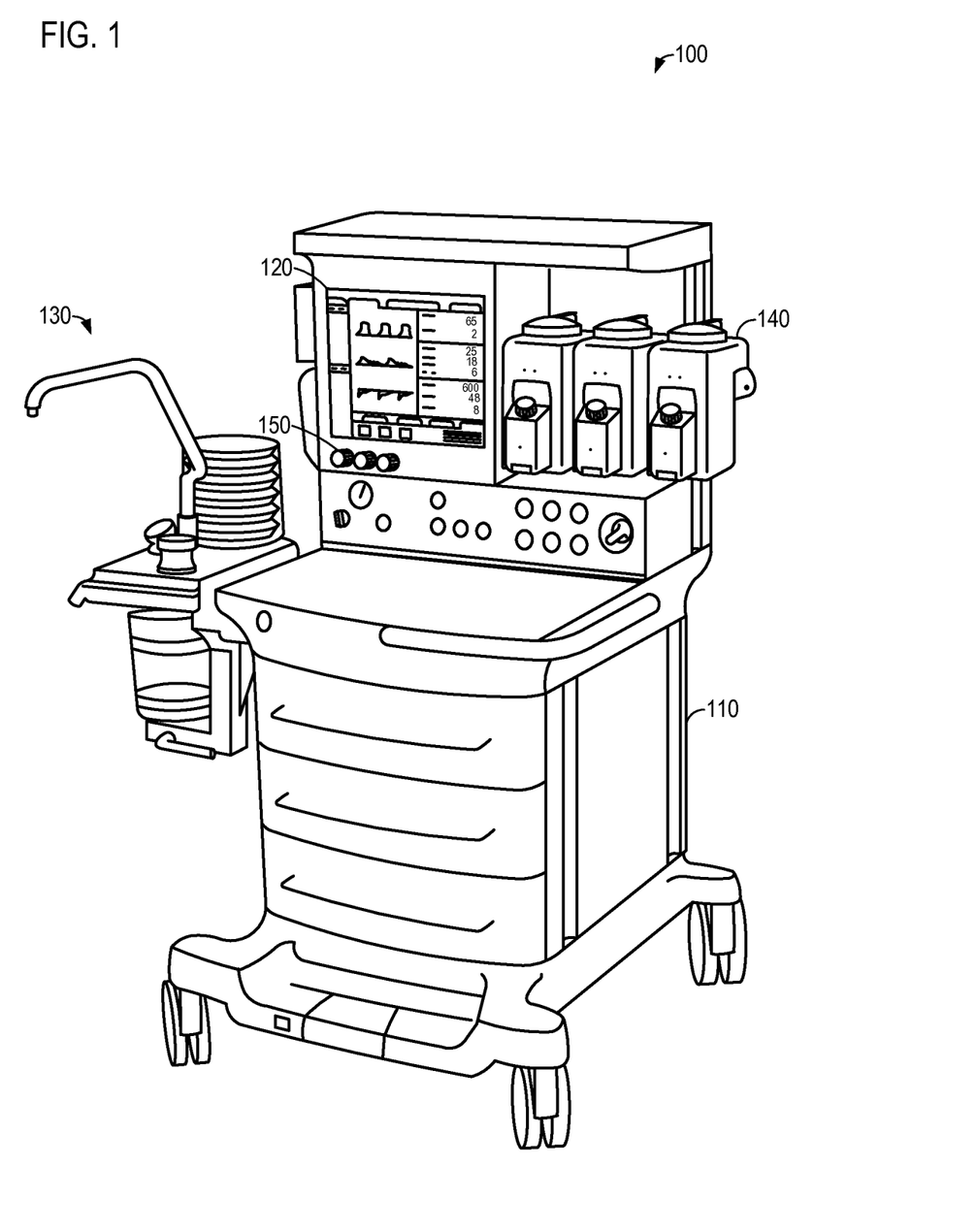
FIG. 1 illustrates an anesthesia machine configured with electronic gas flow controls with integrated manual backup flow controls.

FIG. 1 illustrates an anesthesia machine 100 configured with electronic gas flow controls with integrated manual backup flow controls. As illustrated, the anesthesia machine may include a breathing system 130, anesthetic gas vaporizers 140, and/or other components of an anesthetic delivery system. The anesthesia machine may include a cart 110 for portability. An electronic display 120 may provide information regarding the flow rate and/or anesthetic delivery process to a practitioner. Additionally, the electronic display 120 may be configured as a touch sensitive display to allow a practitioner to provide a selection of a flow rate.

According to various embodiments, three flow selectors 150, illustrated as knobs, may serve as inputs to allow for electronic flow control of three gases when the anesthesia machine 100 is in an electronic mode. The three flow selectors 150 may also serve as inputs to allow for manual flow control of the three gases when the anesthesia machine 100 is in a manual mode.

Figure 2:
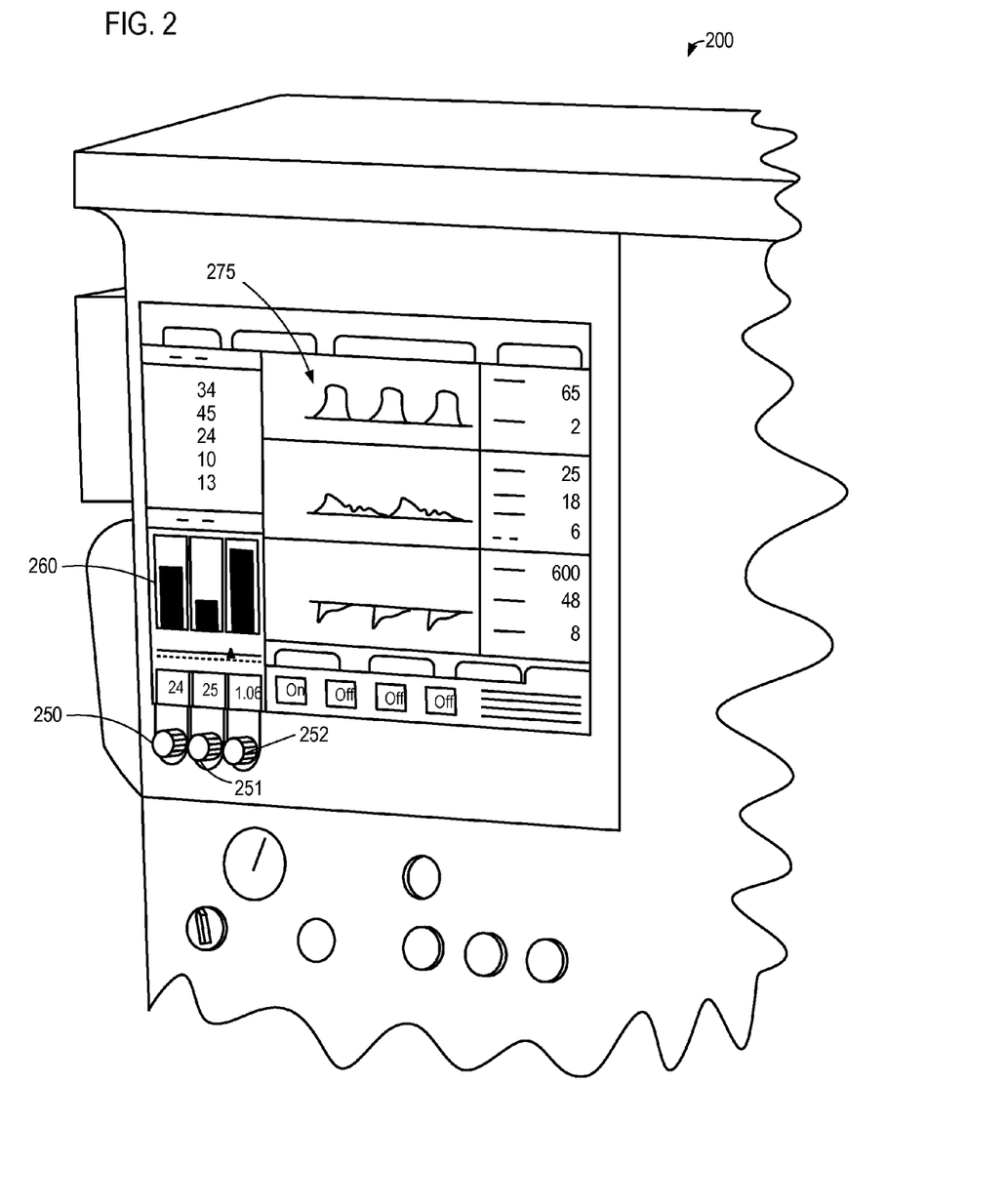
FIG. 2 illustrates a close-up view of electronic flow selector knobs configured to function as manual flow selector knobs in the event power is unavailable or lost.

FIG. 2 illustrates a close-up view 200 of electronic flow selector knobs 250, 251, and 252 configured to function as manual flow selector knobs in a manual mode. As illustrated, a display 275 may provide various telemetry data associated with a patient to a practitioner. The display 275 may also provide touch control of the anesthesia machine. The flow selector knob 250 may be used to control the flow of oxygen, the flow selector knob 251 may be used to control the flow of nitrous oxide, and the flow selector knob 252 may be used to control the flow of air. A practitioner may manually rotate each of the flow selector knobs 250, 251, and 252 in order to select a desired flow of one or more of the available gases.

Flow rate displays 260 may indicate a selected flow rate of each of the gases associated with each of the knobs 250, 251, and 252. In some embodiments, the flow rate displays 260 may be electronic. In other embodiments, the flow rate displays 260 may be mechanical, such that they are capable of displaying an associated flow rate even in a manual mode. In other embodiments, the flow rate displays 260 may be electronic or electronically enhanced when in an electronic mode and mechanical when in a manual mode.

While the illustrated embodiments show three flow selector knobs 250, 251, and 252, any number of flow selectors and associated gases may be utilized. For example, a flow control system may be configured to allow for the electronic and backup manual control of one, two, three, four . . . or N number of gases or liquids. In some embodiments, more than one knob may be configured to control the flow rate of the same gas.

A gas flow control system, according to any of the various embodiments described herein, may be used in conjunction with any of a wide variety of applications. In the illustrated embodiments, the gas flow control systems are shown as parts of anesthesia delivery systems. In such embodiments, the combined flow of one or more gases may be injected or otherwise infused with anesthesia, such as via a vaporizer, for a controlled delivery of the anesthesia and/or the one or more gases to a patient.

Figure 3:
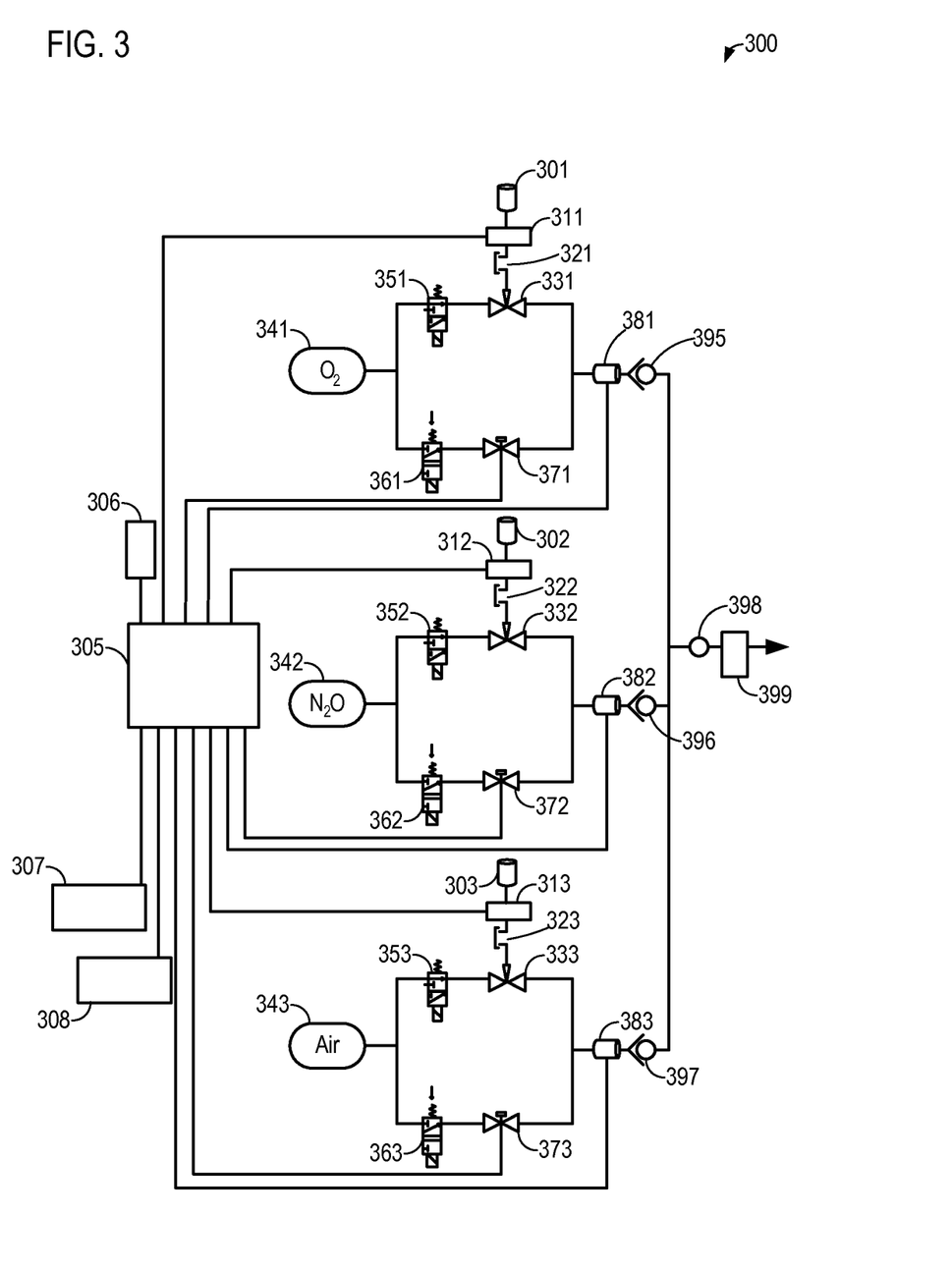
FIG. 3 illustrates a diagram of an anesthesia delivery system in which electronic controls for oxygen, nitrous oxide, and air include manual backup controls.

FIG. 3 illustrates a diagram of an anesthesia delivery system 300 in which electronic controls for oxygen, nitrous oxide, and air include manual backup control features. A first manually rotatable knob 301 may be used to control the flow rate of a first gas, oxygen 341. A second manually rotatable knob 302 may be used to control the flow rate of a second gas, nitrous oxide 342. A third manually rotatable knob 303 may be used to control the flow rate of a third gas, air 343.

In an electronic mode, the anesthesia delivery system 300 may utilize a controller 305. The controller 305 may implement various functions associated with electronic control of the flow rates of one or more gases, receiving inputs from a practitioner via various peripheral devices, and/or displaying information, such as telemetry data associated with a patient, to a practitioner and/or patient. In some embodiments, electronic control of the flow rates of one or more gases may be implemented via hardware, firmware, and/or software and may be distinct from other electronic controls, microprocessors, and/or the like of the anesthesia delivery system.

In an electronic mode, the anesthesia delivery system 300 may also utilize a touch pad 306 to receive inputs from a practitioner and/or patient. The anesthesia delivery system 300 may also utilize a display 307 and/or associated touch screen 308 when in an electronic mode. Controls may be available to allow the practitioner to control the amount of anesthesia delivered to a patient.

In an electronic mode, a flow rate selection made via one or more of the manually rotatable knobs 301, 302, and 303 may be electronically encoded by an associated encoder 311, 312, and 313. The controller 305 may received the electronically encoded selection(s) from the encoder(s) 311, 312, and 313. The controller 305 may then transmit corresponding control signals to electronic proportional valves 371, 372, and 373 associated with each of the gases 341, 342, and 343.

In an electronic mode, the normally-closed valves 361, 362, and 363 are opened such that the gases 341, 342, and 343 are allowed to flow to the electronic proportional valves 371, 372, and 373. The normally-opened valves 351, 352, and 353 may be closed in an electronic mode to prevent the gases 341, 342, and 343 from flowing through mechanically operated needle valves 331, 332, and 333. Clutches 321, 322, and 323 may disengage the manually rotatable knobs 301, 302, and 303 from the needle valves 331, 332, and 333 to prevent manual adjustment of the needle valves 331, 332, and 333 when the gas flow rate system is in an electronic mode. The gases 341, 342, and 343 may flow through the normally-closed valves 361, 362, and 363 and through the electronic proportion valves 371, 372, and 373 at a flow rate specified by the manually controllable knobs 301, 302, and 303.

In the event power is unavailable, power is lost, an electronic malfunction occurs, and/or a user selects a manual mode, the flow rate of the gases 341, 342, and 343 may be manually controlled by the manually rotatable knobs 301, 302, and 303. In a manual mode, the controller 305, the touchpad 306, the display 307, the touch screen 308, and the encoders 311, 312, and 313 may not function.

According to various embodiments, the manually rotatable knobs 301, 302, and 303 may continue to allow for the uninterrupted control of the flow rate of the gases 341, 342, and 343. The normally-closed valves 361, 362, and 362 may close when the system is in a manual mode. The normally-open valves 351, 352, and 353 may remain in an open state when in a manual mode, allowing gases 341, 342, and 343 to flow to the mechanically operated needle valves 331, 332, and 333. In the manual mode, the clutches 321, 322, and 323 may engage the manually rotatable knobs 301, 302, and 303 with the needle valves 331, 332, and 333, such that the manually rotatable knobs 301, 302, and 303 are operable to manually control the flow of the associated gases 341, 342, and 343 through the needle valves 331, 332, and 333.

Whether electronically controlled in an electronic mode or manually controlled in a manual mode, the flow rate of each gas 341, 342, and 343 may be measured by a flow rate measurement device 381, 382, and 383. Check valves 395, 396, and 397 may prevent backflows of the gases 341, 342, and 343. A total-flow measurement device 398 may measure the combined flow of the gases 341, 342, and 343. A vaporizer 399 may inject one or more anesthetics into the gases 341, 342, and 343.

Figure 4:
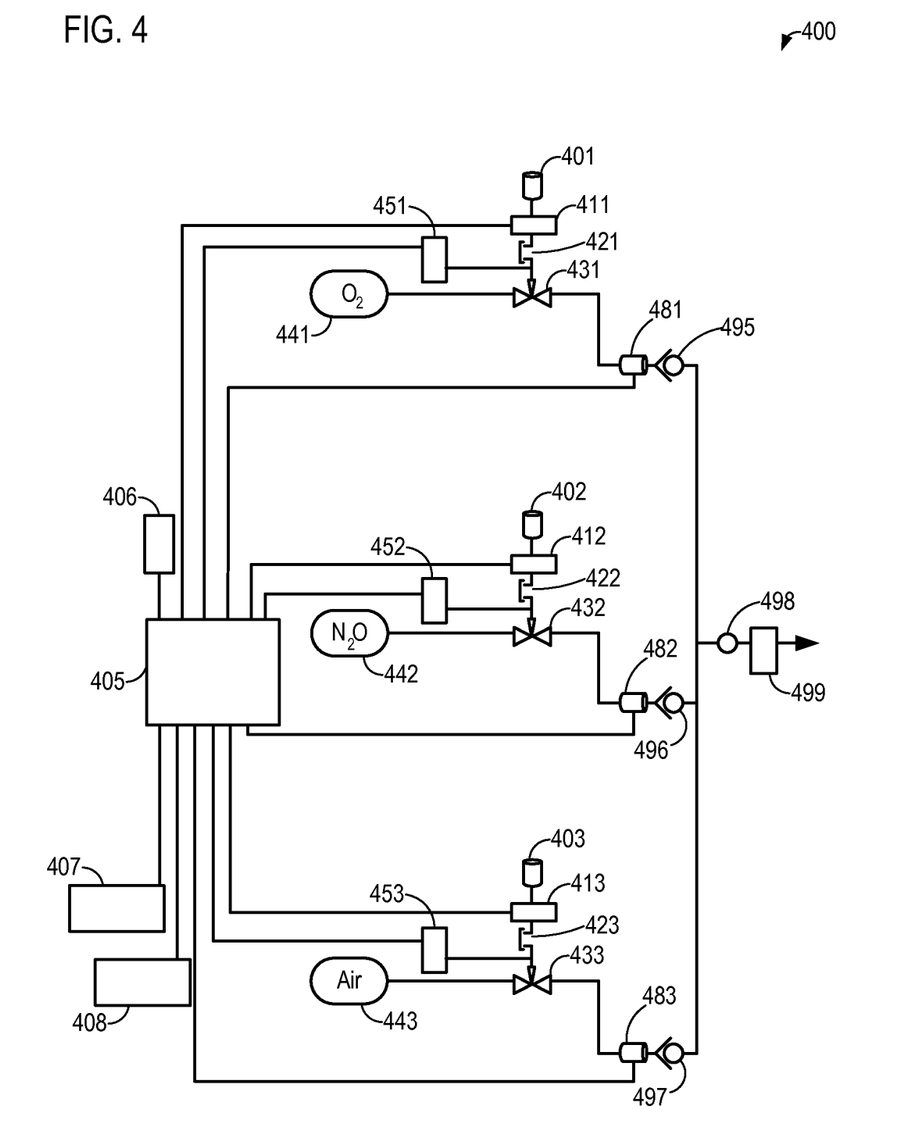
FIG. 4 illustrates an alternative embodiment of an anesthesia delivery system in which the electronic controls for each of oxygen, nitrous oxide, and air utilize a stepper motor in combination with a mechanically operated needle valve.

FIG. 4 illustrates an alternative embodiment of an anesthesia delivery system 400 in which the electronic controls for each of oxygen 441, nitrous oxide 442, and air 443 utilize stepper motors 451, 452, and 453 in combination with manually actuated needle valves 431, 432, and 433. First, second, and third manually rotatable knobs 401, 402, and 403 may be used to control the flow rate of oxygen 441, nitrous oxide 442, and air 443, respectively, whether or not the anesthesia delivery system 400 is in an electronic mode or a manual mode.

In an electronic mode, the anesthesia delivery system 400 may utilize a controller 405 to electronically control the flow rate of gases and/or liquids. The controller 405 may implement various functions associated with electronic control of the flow rates of one or more of the gases 441, 442, and 443, receiving inputs from a practitioner via various peripheral devices, and/or displaying information, such as telemetry data associated with a patient, to a practitioner and/or patient. For example, the anesthesia delivery system 400 may also utilize a touch pad 406 to receive inputs from a practitioner and/or a patient. The anesthesia delivery system 400 may also utilize a display 407 and/or a touch screen 408 when in an electronic mode. The electronic control of the flow rates of one or more gases may be implemented via hardware, firmware, and/or software distinct from other electronic controls, microprocessors, and/or the like.

In an electronic mode, a flow rate selection made via one or more of the manually rotatable knobs 401, 402, and 403 may be electronically encoded by an associated encoder 411, 412, and 413. The controller 405 may receive the electronically encoded selection(s) from the encoder(s) 411, 412, and 413. The controller 405 may then transmit a corresponding control signal to one or more of the stepper motors 451, 452, and 453, respectively. The stepper motors 451, 452, and 453 may adjust the needle valves 431, 432, and 433 to control the flow of each of the gases 441, 442, and 443.

For example, in an electronic mode, a manual adjustment of manually rotatable knob 401 by a practitioner may be encoded by the encoder 411. The controller 405 may then send a control signal to the stepper motor 451 in order to cause the stepper motor 451 to adjust the flow rate of oxygen 441 through the needle valve 431. The clutches 421, 422, and 423 may disengage the manually rotatable knobs 401, 402, and 403 from the needle valves 431, 432, and 433 to prevent manual adjustment of the needle valves 431, 432, and 433 when the gas flow rate system is in an electronic mode.

In a manual mode, or in the event of an electronic malfunction, the controller 405, the touchpad 406, the display 407, the touch screen 408, the encoders 411, 412, and 413, and/or the stepper motors 451, 452, and 453 may not function and/or may function incorrectly. According to various embodiments, the manually rotatable knobs 401, 402, and 403 may continue to allow for the uninterrupted control of the flow rate of the gases 441, 442, and 443. The clutches 421, 422, and 423 may engage the manually rotatable knobs 401, 402, and 403 with needle valves 431, 432, and 433, such that the manually rotatable knobs 401, 402, and 403 are operable to manually control the flow of the associated gases 441, 442, and 443 through the needle valves 431, 432, and 433.

In some embodiments, clutches may disengage the stepper motors 451, 452, and 453 from the needle valves 431, 432, and 433. In some embodiments, a diversion valve or valve combination may direct a flow of a gas to different valves based on whether or not the system is in an electronic or manual mode.

Whether electronically controlled in an electronic mode or manually controlled in a manual mode, the flow rate of each gas 441, 442, and 443 may be measured by a flow rate measurement device 481, 482, and 483. The total flow rate may be displayed on the display 407 in an electronic mode or via a mechanical display in a manual mode. Check valves 495, 496, and 497 may prevent backflows of gases 441, 442, and 443. A total-flow measurement device 498 may measure the combined flow rate of the gases 441, 442, and 443. A vaporizer 499 may inject, or otherwise allow for the vaporization of, one or more anesthetics into the gases 441, 442, and 443.

Figure 5A:
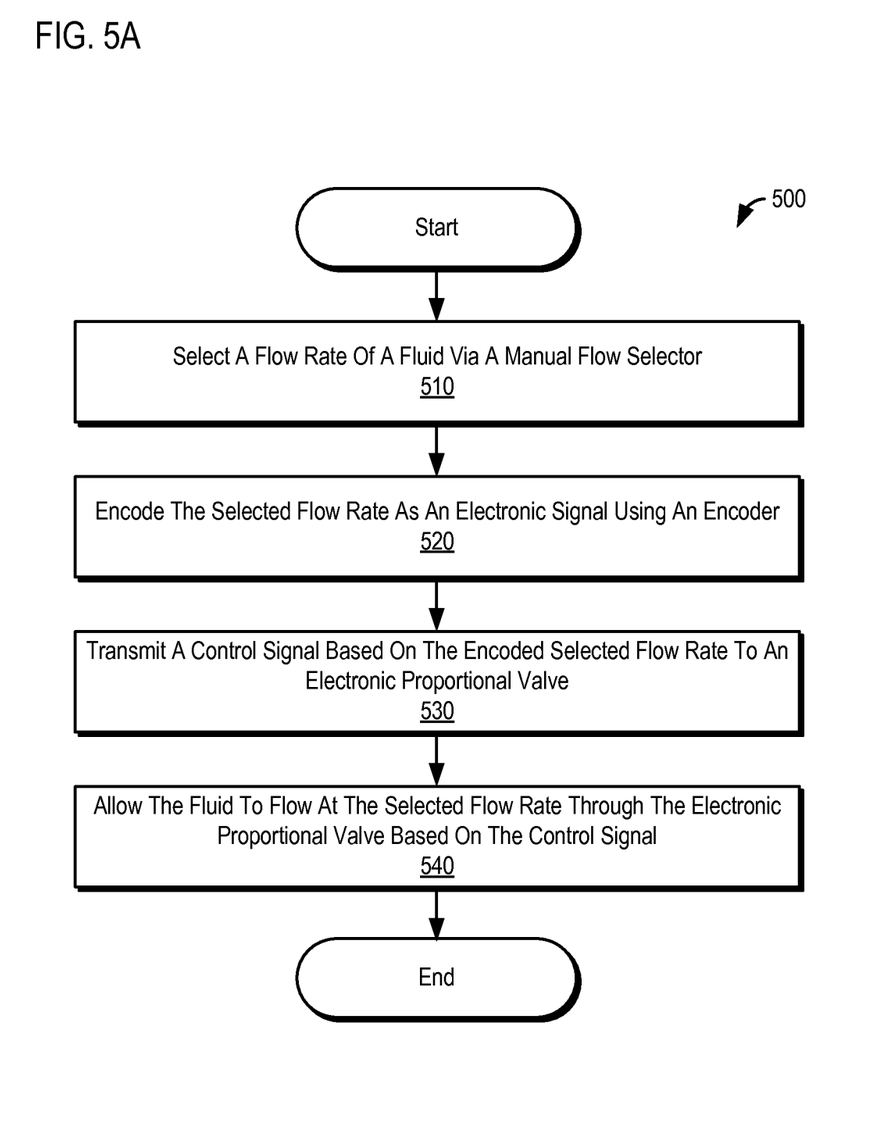
FIG. 5A illustrates a flow chart of a method for electronically controlling the flow rate of a fluid when a flow control system is in an electronic mode.

FIG. 5A illustrates a flow chart of a method 500 for electronically controlling the flow rate of a fluid when in an electronic mode. Initially, an operator may select a flow rate of a fluid via a manual flow selector, such as a knob, slider, button, touch screen, or switch, at 510. An encoder may encode the selected flow rate as an electronic signal, at 520. A controller may receive the encoded selection of a flow rate and transmit a control signal based on the encoded selected flow rate to an electronic proportional valve, at 530. The electronic proportional valve may allow the fluid to flow at the selected flow rate through the electronic proportional valve based on the control signal, at 540.

In an electronic mode, a fluid flow control system may electronically control the flow of a fluid. Electronic displays, information charts, inputs, and/or outputs associated with the flow rate of the fluid may be provided to a practitioner. In the event the system is put in a manual mode and/or an electronic component malfunctions, a backup manual control system may be available utilizing the same manual flow selectors.

Figure 5B:
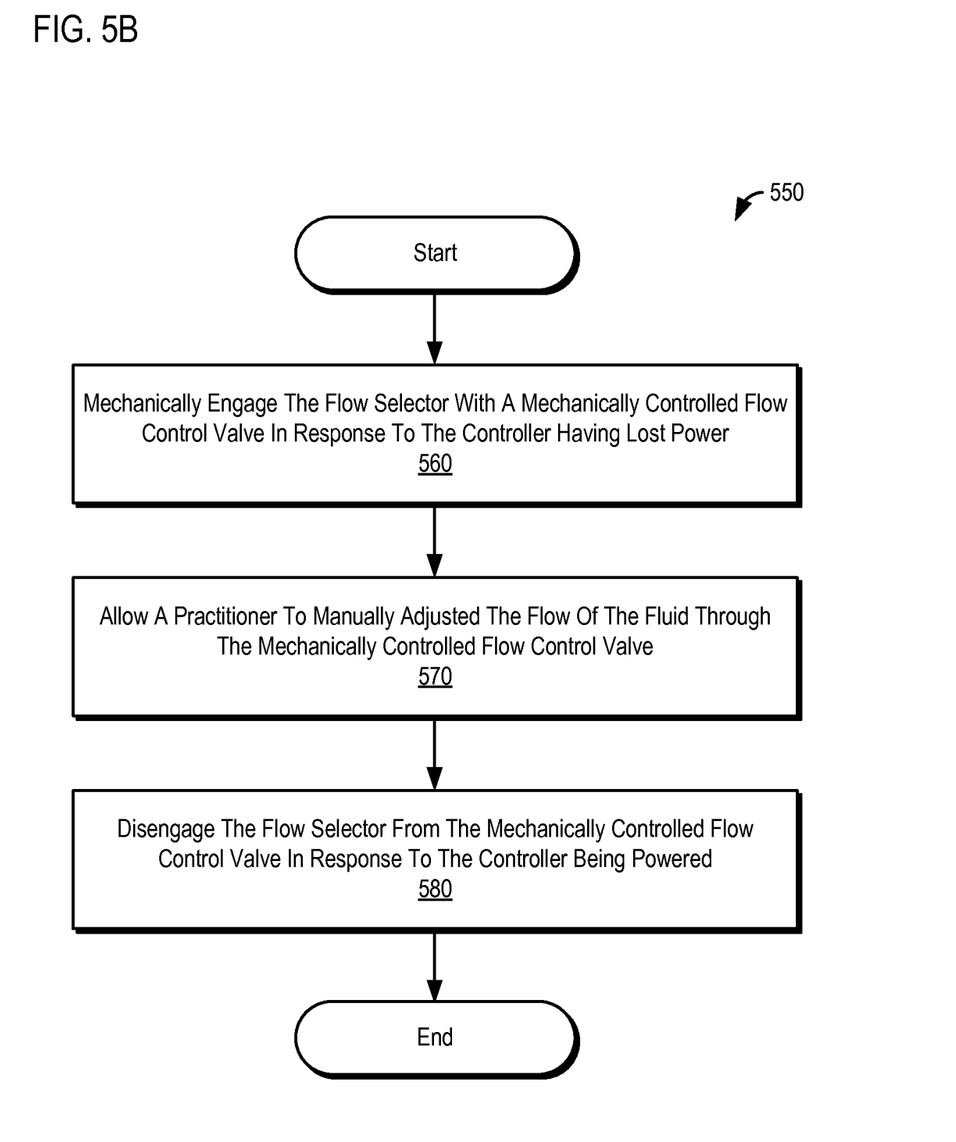
FIG. 5B illustrates a flow chart of a method for providing backup manual control of the flow rate of the fluid when the flow control system is in a manual mode.

FIG. 5B illustrates a flow chart of a method 550 for providing backup manual control of the flow rate of the fluid when in a manual mode. In a manual mode, a clutch or other engagement device may mechanically engage the flow selector with a mechanically controlled flow control valve, at 560. For example, a clutch may engage a rotatable knob with a mechanical actuator of a needle valve. A practitioner may then manually adjust the flow of the fluid through the mechanically controlled flow control valve, at 570. In the event power is made available and/or the system otherwise enters an electronic mode, the clutch may disengage the flow selector from the mechanically controlled flow control valve, at 580, returning the system to an electronically controlled state as described in FIG. 5A.

This disclosure has been made with reference to various exemplary embodiments, including the best mode. However, those skilled in the art will recognize that changes and modifications may be made to the exemplary embodiments without departing from the scope of the present disclosure. While the principles of this disclosure have been shown in various embodiments, many modifications of structure, arrangements, proportions, elements, materials, and components may be adapted for a specific environment and/or operating requirements without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. The scope of the present invention should, therefore, be determined by the following claims.

What is claimed is:

1. A fluid flow control system, comprising:
   a mechanical flow control valve configured to selectively receive a first fluid from a first fluid supply;
   an electronic flow control valve configured to selectively receive the first fluid from the first fluid supply;
   a diversion valve system configured to:
     prevent the flow of the first fluid to the mechanical flow control valve and allow the flow of the first fluid to the electronic flow control valve when the fluid flow control system is in an electronic mode; and
     allow the flow of the first fluid to the mechanical flow control valve and prevent the flow of the first fluid to the electronic control valve when the fluid flow control system is in a manual mode;
   a manually operated flow selector configured to allow for a selection of a flow rate of the first fluid from the fluid supply;
   an encoder configured to electronically encode the selection made via the flow selector;
   a controller configured to transmit a control signal to the electronic flow control valve to cause the electronic flow control valve to allow the first fluid to flow at the selected flow rate; and
   an engagement device configured to engage the flow selector with the mechanical flow control valve when the fluid flow control system is in a manual mode, such that the flow selector is operable to manually control the flow of the first fluid through the mechanical flow control valve.

2. The fluid flow control system of claim 1, further comprising a vaporizer configured to inject an anesthetic into the first fluid, and wherein the first fluid comprises a gas.

3. The fluid flow control system of claim 1, wherein the electronic control valve comprises an electronic proportional valve.

4. The fluid flow control system of claim 1, wherein the manual control valve comprises a needle valve.

5. The fluid flow control system of claim 1, wherein the manual control valve comprises a needle valve and the electronic control valve comprises a stepper motor configured to electronically control the needle valve.

6. The fluid flow control system of claim 1, wherein the diversion valve system comprises:
- a normally open valve configured to allow the flow of the first fluid to the mechanical flow control valve when the fluid flow control system is in a manual mode; and
- a normally closed valve configured to prevent the flow of the first fluid to the electronic control valve when the fluid flow control system is in a manual mode.

7. The fluid flow control system of claim 1, wherein the flow selector comprises a rotatable knob and the encoder comprises a rotary encoder.

8. The fluid flow control system of claim 1, wherein the controller comprises a hardware controller.

9. The fluid flow control system of claim 1, wherein the controller comprises a field-programmable gate array.

10. The fluid flow control system of claim 1, wherein the engagement device comprises a clutch.

11. The fluid flow control system of claim 1, wherein the first fluid comprises one or more of oxygen, nitrous oxide, and air.

12. The fluid flow control system of claim 1, further comprising:
- a second mechanical flow control valve configured to selectively receive a second fluid from a second fluid supply;
- a second electronic flow control valve configured to selectively receive the second fluid from the second fluid supply;
- a second diversion valve system configured to:
  - prevent the flow of the second fluid to the second mechanical flow control valve and allow the flow of the second fluid to the second electronic flow control valve when the fluid flow control system is in an electronic mode; and
  - allow the flow of the second fluid to the second mechanical flow control valve and prevent the flow of the second fluid to the second electronic control valve when the fluid flow control system is in a manual mode;
- a second manually operated flow selector configured to allow for a selection of a flow rate of the second fluid from the second fluid supply;
- a second encoder configured to electronically encode the selection made via the second flow selector;
- a second engagement device configured to engage the second flow selector with the second mechanical flow control valve when the fluid flow control system is in a manual mode, such that the second flow selector is operable to manually control the flow of the second fluid through the second mechanical flow control valve;
- a third mechanical flow control valve configured to selectively receive a third fluid from a third fluid supply;
- a third electronic flow control valve configured to selectively receive the third fluid from the third fluid supply;
- a third diversion valve system configured to:
- prevent the flow of the third fluid to the third mechanical flow control valve and allow the flow of the third fluid to the third electronic flow control valve when the fluid flow control system is in the electronic mode; and
- allow the flow of the third fluid to the third mechanical flow control valve and prevent the flow of the third fluid to the third electronic control valve when the fluid flow control system is in the manual mode;
- a third manually operated flow selector configured to allow for a selection of a flow rate of the third fluid from the third fluid supply;
- a third encoder configured to electronically encode the selection made via the third flow selector;
- a third engagement device configured to engage the third flow selector with the third mechanical flow control valve when the fluid flow control system is in the manual mode, such that the third flow selector is operable to manually control the flow of the third fluid through the third mechanical flow control valve, and
- wherein the controller is configured to transmit control signals to each of the electronic flow control valves to cause each respective electronic flow control valve to allow the respective fluids to flow at the selected flow rates, respectively.

13. The fluid flow control system of claim 12, wherein the first fluid comprises oxygen, the second fluid comprises nitrous oxide, and the third fluid comprises air.

* * * * *